United States Patent
Ross et al.

(10) Patent No.: US 9,933,847 B1
(45) Date of Patent: *Apr. 3, 2018

(54) SYSTEM AND METHOD FOR PRESENTING VIRTUAL REALITY CONTENT TO A USER BASED ON BODY POSTURE

(71) Applicant: VISIONARY VR, INC., Los Angeles, CA (US)

(72) Inventors: Jonathan Michael Ross, Santa Monica, CA (US); Gil Baron, Los Angeles, CA (US); Cosmo Raleigh Scharf, Los Angeles, CA (US); Luke Russell Patterson, Los Angeles, CA (US); Jake Richard Parker, Burbank, CA (US); John Kanikula Peters, Los Angeles, CA (US)

(73) Assignee: Visionary VR, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/601,872

(22) Filed: May 22, 2017

Related U.S. Application Data

(63) Continuation of application No. 14/736,183, filed on Jun. 10, 2015, now Pat. No. 9,665,170.

(51) Int. Cl.
*G09G 5/00* (2006.01)
*G06F 3/01* (2006.01)
*G06T 19/00* (2011.01)
*H04N 13/04* (2006.01)

(52) U.S. Cl.
CPC ............ *G06F 3/011* (2013.01); *G06T 19/006* (2013.01); *H04N 13/0429* (2013.01); *H04N 13/0481* (2013.01)

(58) Field of Classification Search
CPC ..... G06F 3/012; G06F 3/011; H04N 13/0429; H04N 13/0481; G06T 19/006
USPC .............................................................. 345/8
See application file for complete search history.

(56) References Cited

U.S. PATENT DOCUMENTS

| 9,392,212 | B1 | 7/2016 | Ross |
| 2009/0256904 | A1 | 10/2009 | Krill |
| 2011/0102552 | A1 | 5/2011 | Diehl |
| 2011/0320116 | A1 | 12/2011 | DeMaio |

(Continued)

OTHER PUBLICATIONS

Hubber, Kadhim, 'Are you ready for the virtual reality revolution?' The Guardian, Aug. 2, 2014, 5 pages.

*Primary Examiner* — Adam J Snyder
(74) *Attorney, Agent, or Firm* — Sheppard Mullin Richter & Hampton LLP

(57) ABSTRACT

A system and/or method that uses a body posture of a user to determine and modulate a content mode of a virtual reality system. The content mode may define the manner in which virtual reality content is presented to the user and/or the manner in which the user interacts with the virtual reality content. The user's body posture and/or a change in body posture may cause the content mode and/or the virtual reality content to change accordingly. In some implementations, primary content may be presented to the user according to a first content mode in response to the user sitting. Secondary virtual reality content may be presented to the user according to the second content mode in response to the user standing. As such, a user may initiate a change in the virtual reality content and/or the content mode by standing from a sitting posture and/or sitting from a standing posture.

22 Claims, 6 Drawing Sheets

(56) References Cited

U.S. PATENT DOCUMENTS

| | | |
|---|---|---|
| 2012/0127169 A1 | 5/2012 | Barcay |
| 2012/0133884 A1 | 5/2012 | Ishida |
| 2012/0212414 A1 | 8/2012 | Osterhout |
| 2012/0299920 A1 | 11/2012 | Coombe |
| 2013/0050260 A1 | 2/2013 | Reitan |
| 2013/0336629 A1 | 12/2013 | Mulholland |
| 2013/0342525 A1 | 12/2013 | Benko |
| 2014/0002443 A1 | 1/2014 | Cunningham |
| 2014/0009476 A1 | 1/2014 | Venkitaraman |
| 2014/0361956 A1 | 12/2014 | Mikhailov |
| 2015/0094142 A1 | 4/2015 | Stafford |
| 2016/0018655 A1 | 1/2016 | Imoto |
| 2016/0027212 A1 | 1/2016 | da Veiga |
| 2016/0054565 A1 | 2/2016 | Izumihara |

SYSTEM AND METHOD FOR PRESENTING VIRTUAL REALITY CONTENT TO A USER BASED ON BODY POSTURE

FIELD OF THE DISCLOSURE

This disclosure relates to a system and method for presenting virtual reality content to a user.

BACKGROUND

Virtual reality headset display devices are known. These devices visually simulate a user's physical presence in virtual spaces. Simulations may include a 360° view of the surrounding virtual space such that the user may turn his head to watch content presented within the virtual space. (Note that the term "he/his" is used generically throughout the application to indicate both male and female.) Typically, virtual reality content is limited to either passive or interactive content because it is difficult for passive and interactive content to co-exist without competing or negating one another. For example, movies and video games typically cannot successfully co-exist because of their antithetical passive and interactive qualities that make creating seamless transitions and cohesive story-telling difficult.

Virtual reality presents a problem for storytellers that want to provide a rich passive experience and for users that may prefer the ability to switch or alternate to an active interaction with the virtual space. Typically, it is difficult for a storyteller to provide a rich story telling experience with seamless transitions between interactive content while managing and/or maintaining the attention of an audience member.

SUMMARY

The present system uses a body posture of a user to determine and modulate a content mode of a virtual reality system. The content mode may define the manner in which virtual reality content is presented to the user. In some implementations, the content mode may define the manner in which the user interacts with the virtual reality content. In some implementations, the manner in which the user interacts with the virtual reality content may include the manner in which the user is limited from interacting with the virtual reality content. The user's body posture and/or a change in body posture may cause the content mode and/or the virtual reality content to change accordingly. For example, the first content mode may be determined responsive to a first body posture of the user being determined. The first content mode may define how primary virtual reality content may be presented to the user. In some implementations, the second content mode may be determined responsive to a second body posture of the user being determined. The second content mode may define how secondary virtual reality content may be presented to the user. The primary content may be presented to the user according to the first content mode in response to the user sitting. The secondary virtual reality content may be presented to the user according to the second content mode in response to the user standing. As such, a user may initiate a change in the virtual reality content and/or the content mode by standing from a sitting posture and/or sitting from a standing posture.

In some implementations, primary virtual reality content may refer to any virtual reality content that is passive and/or presented to a user for viewing from a creator dictated location. The creator dictated location may describe a location relative to the action and/or virtual reality content. Secondary virtual reality content may refer to any virtual reality content with which the user may interact such that the user's actions may impact behaviors of entities represented in the secondary virtual reality content. For example, secondary virtual reality content may include interactive narrative content, game content, and/or exploratory content (e.g., presented responsive to the user interacting with and/or exploring an area of the virtual space).

For example, while the user is sitting, the primary virtual reality content may be presented according to first mode such that a passive experience may be facilitated between the user and the primary virtual reality content. The passive experience may include a viewing experience wherein the user views the primary virtual reality content from a creator dictated location. As such, the primary virtual reality content may include passive virtual reality content. Responsive to the user standing, the virtual reality content presented and/or the content mode may change. While the user is standing, the secondary virtual reality content may be presented according to second mode such that an interactive experience may be facilitated between the user and the secondary virtual reality content. The interactive experience may include a viewing experience wherein the user may interact with and/or view the secondary virtual reality content from a user-directed location and/or viewpoint. As such, the secondary virtual reality content may include interactive virtual reality content.

For the user, sitting to have a passive experience and/or standing to have an interactive experience may be intuitive and functional. For example, sitting may be a passive body posture while standing may be an interactive body posture indicating a user's readiness to interact. Furthermore, providing passive virtual reality content while a user is sitting may enable the storyteller to provide primary content that is richer because the user is located in a somewhat fixed position in the real world and the user's spatial location within the virtual reality content relative to the action and/or virtual reality content may be creator dictated. As such, changing content modes based on body posture enables a seamless, intuitive transition between passive and interactive virtual reality content allowing both to co-exist meaningfully without competing or negating one another. Also, changing content modes based on body posture enables passive and interactive experiences in virtual reality content to mirror real-life. When a person wants to be passive in real-life, he sits or you stand passively and when he wants to interact in real-life, he reaches out, interacts, and/or responds.

One or more aspects of the disclosure relate to a system configured to present virtual reality content to a user. The system may include software components, hardware components, and/or other components operating together to cause the system to function as described herein. For example, the system may enable a content creator (e.g., a storyteller, a filmmaker, a game maker, a game creator, and/or other content creators) to create and provide passive virtual reality content according to a first mode and interactive virtual reality content according to a second mode to an audience member (e.g., a user) wherein the transitions may be seamlessly controlled responsive to the audience member's body posture. The virtual reality content may be presented to the user in a virtual space. The virtual reality content may include primary virtual reality content, secondary virtual reality content, intermediary virtual reality content, and/or other virtual reality content. The virtual reality content may be presented to the user according to a first content mode, a second content mode, a third content mode, and/or other content mode.

The system may be configured such that primary virtual reality content may be displayed to a user while sitting down. Responsive to the user standing up, the content mode may change and the secondary virtual reality content may be provided to the user according to the second content mode. In some implementations, the primary virtual reality content may and/or may not be paused. The secondary virtual reality content and/or other virtual reality content may be displayed to the user. In some implementations, the secondary virtual reality content may include interactive primary virtual reality content, new and/or additional secondary virtual reality content, and/or other secondary virtual reality content.

The system may be configured to determine that the user's body posture has changed. In some implementations, the content mode may switch from the second content mode back to the first content mode when user returns his body posture to sitting (e.g., sits back down). In some implementations, responsive to the user returning his body posture to sitting, the primary virtual reality content may resume according to the first content mode (e.g., automatically). The primary virtual reality content subsequently displayed to the user may be adjusted based on a user's interactive experience with the secondary virtual reality content and/or other information. These features are not limited to the primary virtual reality content. For example, the system may be configured such that secondary virtual reality content may pause when the user sits down and then resumes when the user stands back up. The primary, secondary, intermediary virtual reality content, and/or other virtual reality content may be adjusted based on a user's progression through another (e.g., primary and/or secondary) virtual reality content, interaction with another (e.g., primary and/or secondary) virtual reality content, and/or other information.

In some implementations, the system may comprise one or more of, a sensor, a user interface, a processor, electronic storage, and/or other components. The sensor may be configured to generate output signals conveying information related to body posture of the user and/or other information. The body posture of the user may refer to a physical position in which the user's body and/or a portion of a user's body is oriented. For example, body posture may include one or more of sitting, standing, reclining, kneeling, lifting one or more extremities (e.g., a hands-lifted body posture), laying, squatting, a position of one or more extremities (e.g., hands in lap), a leaning body posture (e.g., forward, back, and/or to the side), a head position posture (e.g., the user turning his head to the side, up, and/or down), and/or other body postures. For example, the first body posture may include sitting and/or the second body posture may include standing. In a second example, the first body posture may include reclining and/or the second body posture may include sitting. In a third example, the first body posture may include standing with the user's hands at his side and/or the second body posture may include the user standing with his hands slightly raised. The examples included herein are not intended to be limiting and the first body posture and/or the second body posture may include any body postures and/or any combination of body postures.

The user interface may include a display and/or other components. The display may be configured to present the virtual reality content to the user. The display may be controlled by the processor to present the virtual reality content to the user according to the content mode such that the presented virtual reality content corresponds with the user's desired experience (e.g., a passive experience and/or an interactive experience). In some implementations, the display may be included in a virtual reality headset worn by the user. The virtual reality headset may include a head mounted display. It should be noted that the description of the display provided herein is not intended to be limiting. Rather, the description of the display is intended to include future evolutions of virtual reality display technology (which may not even be display based, for example). For example, the display may include cameras, technology, and/or systems for augmented reality, holographic technology, and/or other augmented reality components, light field imaging devices that project an image onto the back of a user's retina (e.g., near-eye light field displays, etc.) virtual reality technology that utilizes contact lenses, virtual reality technology that communicates directly with the brain, and/or other display technology.

The processor may be configured to execute computer program components. The computer program components may be configured to enable an expert and/or user to interface with the system and/or provide other functionality attributed herein to the user interface, the sensor(s), the electronic storage, and/or the processor. The computer program components may include a body posture component, a content mode component, a display component, and/or other components.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
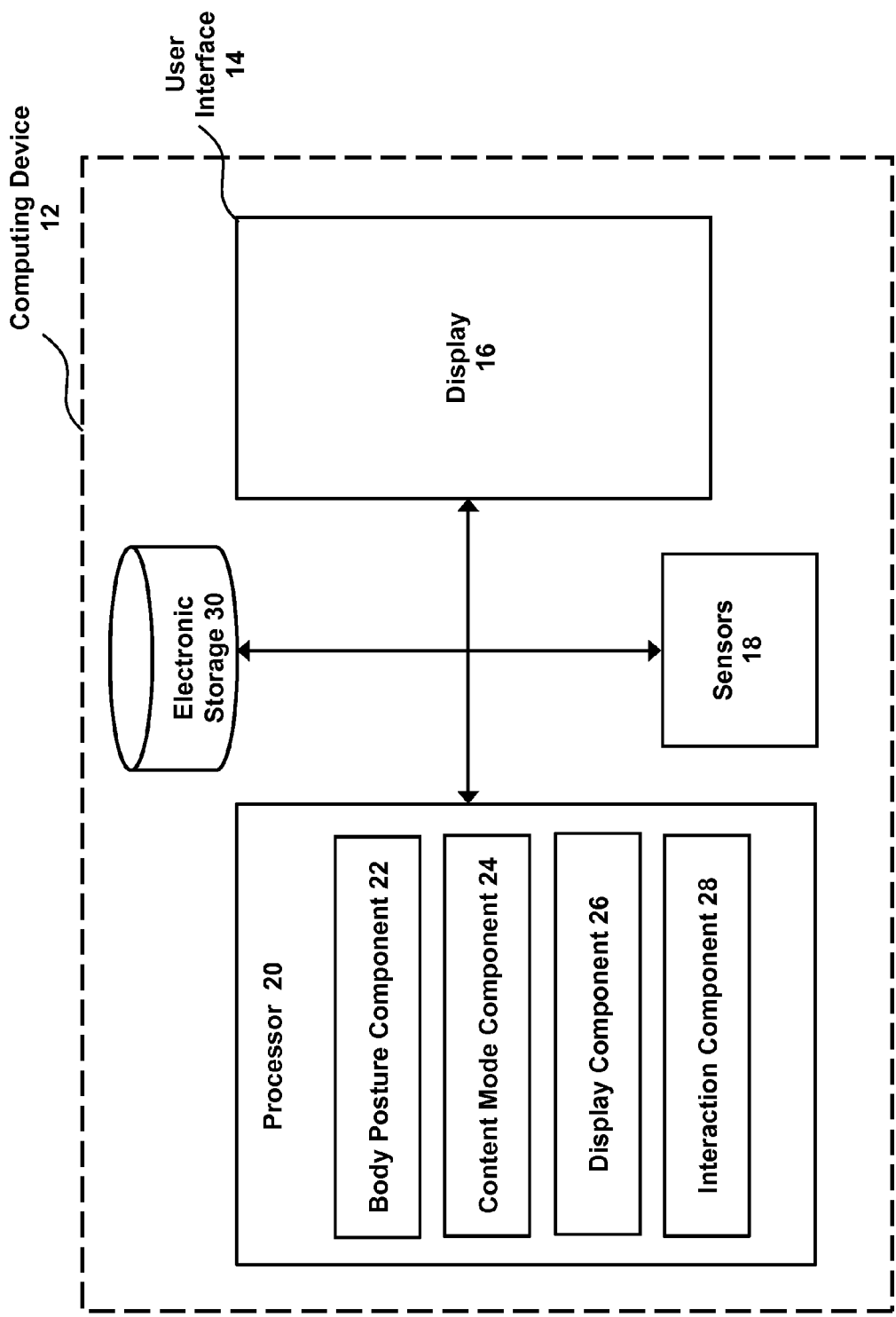
FIG. 1 illustrates a system configured to present virtual reality content to a user, in accordance with an implementation.

The present system may modulate the mode of content between a passive content mode and/or an interactive content mode based on a user's body posture. As such, virtual reality storytelling with interactive capabilities that enable passive and interactive virtual reality content to co-exist without competing and/or negating one another, may be presented to the user. The content modes and/or transitions between content modes may be determined based on the body posture of a user. Responsive to the user having a first body posture, the primary virtual reality content may be presented to the user according to the first content mode. Responsive to the user changing their body posture to a second body posture, the secondary virtual reality content may be presented to the user according to the second content mode. A passive, interactive, and/or other user experience may be facilitated based on the content mode. The user experience between the user and the virtual reality content may be facilitated by causing the display to present the virtual reality content to the user according to the content mode.

The present system may facilitate content governance by a content creator and/or user in one or more ways (e.g., modulating the content mode, presenting virtual reality content according to the content mode, and/or altering other control schemes) based on the body posture of the user. Changes in the body posture of the user may provide an intuitive transition between presenting passive and/or interactive virtual reality content. In the passive content mode, the user's spatial location relative to the action within the virtual reality content and/or to the virtual reality content may be creator dictated. In some implementations, the user may be able to move a small amount (e.g., lean, look around, etc.) from the creator dictated location. In some implementations, the user's movement within the virtual reality content may be more restricted in the primary virtual reality content (e.g., first mode) than in the secondary virtual reality content (e.g., second mode). For example, in the primary virtual reality content, the user may be restricted to a path and in the secondary virtual reality content the user may be able to roam freely and/or more freely than in the primary virtual reality content. As such, the creator may decide when the virtual reality content "cuts" from location to location and/or how a user "moves" through a given location. Thus, the content creator may be able to provide a richer storytelling (e.g., passive experience) via passive virtual reality content according to a passive content mode (e.g., the first mode) because the content creator is in control of the location of the user and/or the progression of the story. To transition between presenting passive virtual reality content to presenting interactive virtual reality content, the system may be configured to switch the content mode. In some implementations, the passive virtual reality content may and/or may not be paused responsive to the user changing body postures (e.g., by standing up). Responsive to the user changing body postures, the system may present interactive virtual reality content according to an interactive content mode (e.g., the second content mode), thus enabling the user to interact with the interactive virtual reality content.

In some implementations, the present system may facilitate a user's ability to choose when to initiate the second content mode (e.g., an interactive content mode) based on his selected body posture, without having to lose track of primary virtual reality content presented according to the first content mode while the user has a first body posture. For example, a user may enjoy multiple areas of different types of experiences (e.g., passive and/or interactive) within a virtual world, while having individual narratives pause when the user changes his body posture to move to another type of experience (e.g., a passive and/or an interactive experience) and then resume when the user changes back to his original body posture. In some implementations, the primary virtual reality content may not be paused and the narrative may continue while the content mode changes to an interactive (e.g., second content mode) and secondary virtual reality content is presented such that a user may interact with the secondary virtual reality content. As such, for example, the user may continue to watch the narrative and/or portions of the narrative while standing. In some implementations, the secondary virtual reality content may include new and/or additional secondary virtual reality content, interactive primary virtual reality content, and/or other secondary virtual reality content.

As used herein, "virtual reality" may refer to what is traditionally considered virtual reality as well as augmented reality and/or other similar concepts. Thus, virtual reality content may include augmented reality content. In some implementations, "virtual reality" may refer to a form of virtual reality/augmented reality hybrid and/or include an aspect and/or ability to view content in an augmented reality way. For example, creators may generate traditional virtual reality content but use augmented reality cameras and/or technology to keep the user's peripheral vision open so they can keep an eye on the physical world around them.

The terms "primary virtual reality content" and "secondary virtual reality content" used herein are not intended to be limiting. The system may include any number of different types of virtual reality content. "Primary" and "secondary" may be used generically throughout this disclosure to represent various different types of virtual reality content. The functionality described herein may be applied to any number of different types (e.g., primary, secondary, etc.) of virtual reality content. In some implementations, primary virtual reality content may refer to any virtual reality content that is passive and/or presented to a user for viewing from a creator dictated location. Secondary virtual reality content may refer to virtual reality content with which the user may interact such that the user's actions may impact behaviors of entities represented in the secondary virtual reality content. For example, secondary virtual reality content may include interactive narrative content, game content, experiential content, and/or exploratory content (e.g., presented responsive to the user interacting with and/or exploring an area of the virtual space). In some implementations, the term virtual reality may include virtual reality as described herein, augmented reality, mixed reality and/or other forms of virtual reality.

FIG. 1 illustrates a system 10 configured to present virtual reality content to a user, in accordance with an implementation. The virtual reality content may be presented to the user in a virtual space. The virtual reality content may be presented to the user according to content modes. The content modes may define the flow of content, the manner in which the virtual reality content is presented to the user, the manner in which the user interacts with the virtual reality content, and/or other controls/information that may affect the user's experience with the virtual reality content. In some implementations, the manner in which the user interacts with the virtual reality content may include the manner in which the user is limited from interacting with the virtual reality content. The virtual reality content may include primary virtual reality content, secondary virtual reality content, an intermediary virtual reality content, and/or other virtual reality content. The primary virtual reality content may be presented to the user according to a first content mode. The secondary virtual reality content may be presented to the user according to a second content mode.

The first content mode may include a passive content mode such that the virtual reality content (e.g., the primary virtual reality content) may be presented to the user for viewing from a creator directed location. In the first content mode, the user may not be able to control and/or affect the flow, direction, and/or progress of the virtual reality content presented (e.g., the primary virtual reality content). In the first content mode, the user's actions and/or experience may be more restricted than in the second content mode. The second content mode may include an interactive content mode such that the virtual reality content may be presented in a manner such that the user may interactively experience (e.g., via moving around, walking, running, flying, exploring, playing, etc.) the virtual reality content. In the second content mode, the user's actions and/or experience may be less restricted than in the first content mode. According to the second content mode, the user's location and/or viewpoint may be user-directed (e.g., change based on the user's interaction). A user-directed location may describe a location relative to the action and/or virtual reality content. In the second content mode, the user may be able to interact with and/or impact behaviors of virtual entities and/or objects represented in the virtual reality content. In some implementations, a user's experience and/or interactions in the second content mode may affect the user's experience in the first content mode.

In some implementations, system 10 may determine a third content mode. The third content mode may include one or more intermediary content modes. The intermediary content mode may define the flow of content, the manner in which the virtual reality content is presented to the user, the manner in which the user interacts with the virtual reality content, and/or other controls/information that may affect the user's experience with the virtual reality content. The intermediary content mode (e.g., the third content mode) may be determined based on the body posture of the user and/or a change in the body posture of the user. In some implementations, as the user changes body postures from the first body posture to the second body posture, an intermediary content mode may be determined. For example, if the user changes his body posture from a lying body posture to a standing body posture, an intermediary content mode may be determined while the user is making the transition from a lying body posture to a standing body posture. In some implementations, the user may have a third body posture that includes an intermediary body posture. For example, a first body posture of the user may be a lying down (e.g., on his back, side, and/or stomach) posture and a second body posture may be a standing posture such that a third body posture (e.g., an intermediary body posture) may include a sitting body posture. Continuing the example, the user may initiate a change in content mode from the first content mode to the intermediary (e.g., third) content mode by changing body postures from a lying body posture to a sitting body posture; and then initiate a change in content mode from the intermediary content mode to the second content mode by changing body postures from a sitting body posture to a standing body posture. In some implementations, intermediary virtual reality content may presented according to the intermediary content mode.

In some implementations, primary virtual reality content may include content dictated for consumption by the user. In some implementations, primary content may include passive virtual reality content. Passive virtual reality content may include content that the user engages with by watching and/or viewing. Passive virtual reality content may not be self-directed by the user such that the passive virtual reality content may not be controllable by the user. In some implementations, the passive virtual reality content may be less controllable and/or more restrictive than the interactive virtual reality content. By way of example, primary virtual reality content may include one or more of a narrative, a story, a movie, and/or other passive virtual reality content. Thus, while experiencing the primary content (e.g., the passive virtual reality content), the user may watch to see what happens in a narrative, change his views and/or fields of view (e.g., look around), lean in one or more directions to alter his viewpoint (e.g., without triggering a change in body postures), and/or use one or more controls/interfaces (e.g., a joystick) to alter his viewpoint. Secondary virtual reality content may include interactive virtual reality content. Interactive virtual reality content may include content that the user interacts with by exploring, playing, conversing, controlling entities within, impacting behaviors of entities within, manipulating objects within, and/or otherwise interacts with. Interactive virtual reality content may be self-directed by the user such that the interactive virtual reality content may be impacted and/or controllable by the user. In some implementations, the interactive virtual reality content may be more controllable and/or less restrictive than the passive virtual reality content. By way of example, secondary virtual reality content may include one or more of interactive narrative content, game content, experiential content, exploratory content, interactive characters and/or objects, and/or other interactive virtual reality content. In some implementations, the secondary virtual reality content may be associated with the primary content.

Intermediary virtual reality content may include one or more of primary virtual reality content, secondary virtual reality content, and/or other virtual reality content. In some implementations, intermediary virtual reality content may include one or more user selectable options that facilitate the transition between primary virtual reality content and secondary virtual reality content. In some implementations, the intermediary virtual reality content may include transition virtual reality content (e.g., slowing down and/or fading in/out of primary and/or secondary virtual reality content, transporting content displaying transportation from one location to another, and/or other intermediary virtual reality content). The primary virtual reality content may or may not be paused responsive to the intermediary virtual reality content being presented. In a non-limiting use example, responsive to the user having a first body posture of lying, the primary virtual reality content presented may simulate flying though and viewing the primary virtual reality content on a creator-dictated flight path. Continuing the non-limiting use example, when the user wants to initiate landing so he can interact with the virtual space and/or virtual reality content, he may change body postures from a lying posture to a sitting posture changing the content mode to the intermediary content mode. Continuing the example, the intermediary virtual reality content and/or the intermediary content mode may provide the user with various landing options (e.g., locations, types/methods of landing, and/or other landing options) and when the user lands within the virtual space, the user may change body postures (e.g., in the real world) from a sitting body posture to a standing body posture to change content modes to the second content mode such that the user may interact (e.g., explore and/or interact at ground level) with the secondary virtual reality content.

By way of a non-limiting use example, a user may be sitting and watching primary virtual reality content according to the first mode. Continuing the example, when the user stands up, the primary virtual reality content may pause and the user may be able to interact with it as secondary virtual reality content (e.g., the user doesn't leave the primary content, it becomes interactive). By way of a second non-limiting use example, a user may be sitting and watching primary content and when the user stands up, the primary virtual reality content may change to include new, different, and/or additional secondary virtual reality content that the user may be able to interact with.

System 10 may be configured such that while the user's body posture corresponds to the first body posture, primary virtual reality content may be displayed to a user according to the first content mode. Responsive to the user changing his body posture (e.g., from sitting to standing), the first content mode may change to the second content mode. At such times the primary virtual reality content may or may not be paused and the secondary virtual reality content may be displayed to the user according to the second content mode. System 10 may be configured to determine that a body posture of the user has changed from a first body posture to a second body posture. In some implementations, for example, changing content modes may cause a variable slow down and/or degree of transition of the virtual reality content based on a progression of the change in body posture. The body posture of the user (e.g., the first body posture, the second body posture, the third body posture, and/or other body postures) may refer and/or correspond to a physical position in which the user's body is oriented. For example, the body posture of the user may include one or more of sitting, standing, reclining, kneeling, lifting one or more extremities (e.g., a hands-lifted body posture), laying, squatting, a position of one or more extremities (e.g., hands in lap), a leaning body posture (e.g., forward, back, and/or to the side), a head position posture (e.g., the user turning his head to the side, up, and/or down), and/or other body postures. For example, the first body posture may include sitting and/or the second body posture may include standing. In some implementations, for example, the first body posture may include standing with the user's hands at his side and/or the second body posture may include the user standing with his hands slightly raised.

In some implementations, system 10 may be configured to determine hand gestures, finger gestures, and/or other forms of body communication. The determined hand gestures, finger gestures, and/or other forms of body communication may be used to switch content modes in system 100, control system 100, control the user's interaction with system 100, and/or for other control schemes of system 100.

By way of a non-limiting example, system 10 may be configured such that the virtual reality content is displayed to the user via a virtual reality headset and/or other head mounted display. In this example, the primary virtual reality content may be passive virtual reality content such as a story (e.g., 2D and/or 3D displayed content; captured video; 2D and/or 3D generated content; digitally created characters, objects, and spaces; and/or algorithmically created content), and/or any other primary virtual reality content displayed to the user. The story and/or other passive virtual reality content may be displayed to the user while the user's body posture corresponds to a first body posture (e.g., the user is sitting). Responsive to the user changing his body posture (e.g., from a sitting posture to a standing posture) and/or otherwise changing body postures, system 10 may be configured to change the content mode and/or virtual reality content presented according to the content mode. The secondary virtual reality content may be determined and/or adjusted by system 10 based on the user's progression through the passive virtual reality content and/or story (e.g., as characters and/or objects of interest are introduced in the story they may be added to the secondary, and/or other virtual reality content). Responsive to the user changing his body posture from the first body posture to the second body posture (e.g., from sitting to standing), the user may then able to interact with in the secondary virtual reality content according to the second mode, and/or based on other information. In some implementations, for example, the user may interact with the secondary virtual reality content and then return his body posture back to the first body posture to return to the content presented back to the story, wherein the story has been adjusted to reflect the user's interaction with the secondary virtual reality content. In some implementations, while a user views primary virtual reality content, system 10 may be configured to display a "pop-up" cue indicating that the ability of the user to interact with the virtual reality content (e.g., secondary virtual reality content) is available in a different (e.g., second) content mode. In some implementations, the "pop-up" cue may indicate that the user should change his body posture to correspond with the cue (e.g., the pop-up may alert the user to stand-up). In some implementations, the "pop-up" cue may highlight one or more objects and/or characters within the virtual reality content.

It should be noted that the word "story" as used herein is not intended to be limiting. It may refer to any passive and/or narrative content and/or experience that system 10 is capable of displaying to a user. By way of non-limiting example, a story may be a movie.

In some implementations, system 10 may be configured such that a user may create, customize, and/or adjust the virtual reality content, the content modes, the body postures used to determine the content modes, and/or other characteristics of system 10. The body posture of the user may be used, in some implementations, to alter other control schemes and/or characteristics of the virtual reality content, the content mode, the virtual space, and/or other characteristics and features of system 10.

In some implementations, system 10 may comprise one or more of a user interface 14 (which may include a display 16 and/or other components as described herein), sensor(s) 18, processor(s) 20, electronic storage 30, and/or other components. In some implementations, one or more components of system 10 may be included in a single computing device 12. In some implementations, computing device 12 may be associated with the user. For example, computing device 12 may be owned by the user, carried by the user, operated by the user, and/or associated with the user in other ways. Computing device 12 may include communication lines, or ports to enable the exchange of information with a network, and/or other computing platforms. Computing device 12 may include a plurality of hardware, software, and/or firmware components operating together to provide the functionality attributed herein to computing device 12. Computing device 12 may include, for example, a cellular telephone, a smartphone, a laptop, a tablet computer, a desktop computer, a television set-top box, a smart TV, a gaming console, a virtual reality headset, a head mounted display, and/or other devices. In some implementations, individual components of system 10 (e.g., display 16, sensor(s) 18) may be coupled to (e.g., wired to, configured to wirelessly communicate with) computing device 12 without being included in computing device 12.

In some implementations, computing device 12 may include one or more components (e.g., hardware and/or software) configured to facilitate tracking the body posture of a user and/or other physical user movements for use by system 10. This may include, for example, rotational, body postural, and/or other types of user body tracking used in virtual reality experiences. System 10 may be configured such that a body tracking system (e.g., a system configured for body postural tracking of the body such as head tracking, finger tracking, hand tracking, arm tracking, leg tracking, trunk tracking, etc. which may be an optical and/or camera based MOCAP system and/or a system that does not require a camera, a mechanical system, an inertial system, an acoustic system, a magnetic system, an optical system, resonance, and/or a radar system) and/or other devices (e.g., controllers) may be used to determine a body posture of a user and/or other physical movement information for simulating a user's interaction with the virtual space and/or virtual reality content. This may include components configured to generate information related to a user's brain waves in real time that can be used by system 10 to control one or more aspects of the virtual space.

In some implementations, system 10 and sensor(s) 18 may determine one or more body postures via a body tracking system according to one or more implementations of tracking technology. In some implementations, the body tracking system, system 10, and/or sensor(s) 18 may include hardware that captures different types of video, (e.g., sometimes in combination with depth sensors) which is processed by system 10 to determine posture. In some implementations, the body tracking system, system 10, and/or sensor(s) 18 may include hardware sensors that communicate spatial location information via a wired and/or wireless methods which processed by system 10 to determine posture. In some implementations, the body tracking system, system 10, and/or sensor(s) 18 may include tracking marks on controllers and/or wearables that work with system 10 to communicate spatial location via reflective dots that are hit with lasers and/or other light based technology from multiple angles, and processed by system 10 to triangulate location. The implementations provided herein are not intended to be limiting and are intended to include future evolutions of tracking technology.

Figure 3:
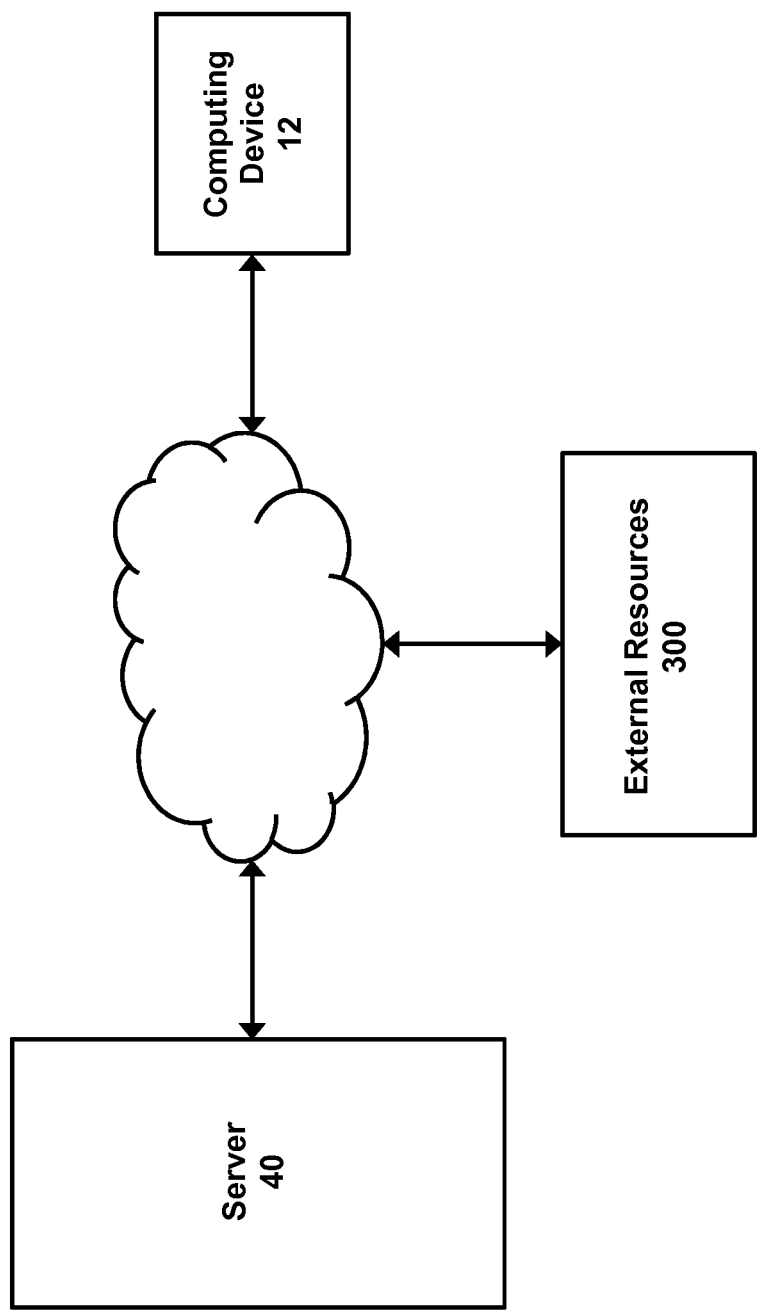
FIG. 3 illustrates a server configured to communicate with a computing device via a network, in accordance with an implementation.

In some implementations, system 10 may include and/or be configured to integrate and/or be used with one or more motion simulators (see e.g., external resources 300 in FIG. 3). The motion simulators may simulate camera movement (e.g., creator-dictated camera movement). For example, a motion simulator may include a motion simulated chair from which the user may watch and/or view the primary virtual reality content. In some implementations, motion simulators may include a floor and/or platform that the user may walk, jog, and/or run around on to interact with the secondary virtual reality content in the interactive (e.g., second) content mode. For example, the floor and/or platform may include an omnidirectional treadmill.

Figure 2:
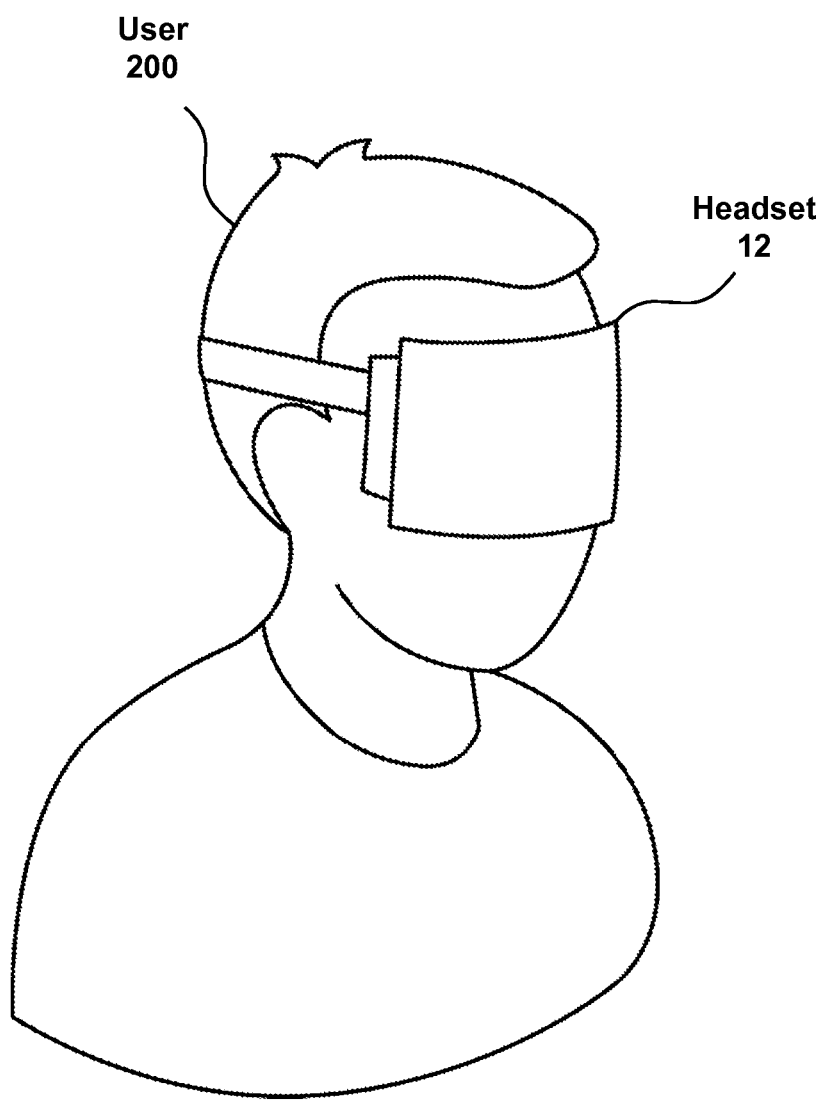
FIG. 2 illustrates a virtual reality headset computing device, in accordance with an implementation.

For example, in FIG. 2, computing device 12 is illustrated as a virtual reality headset that is worn on the head of a user 200. The virtual reality content may be presented to the user in a virtual space via a display included in the headset. The virtual reality headset may be configured such that a perception of a three-dimensional space is created by two stereoscopic movies, one generated for each eye, which are each being rendered in real time and then displayed. The convergence of these two movies in real time—one image to each eye (along with how those views are reactive to viewer head rotation and body posture in space)—may create a specific kind of immersive 3D effect and/or a sensation of presence in a virtual world. Presenting the virtual reality content to the user in the virtual space may include presenting one or more views of the virtual space to the user. In some content modes (e.g., the second content mode), users may participate in the virtual space by interacting with content presented to the user in the virtual space (e.g., the secondary virtual reality content).

The content presented to the user (e.g., the primary virtual reality content, the secondary virtual reality content, the intermediary virtual reality content, and/or other virtual reality content) may include one or more of movies, stories, performances, virtual events, characters, objects, settings, collaborative projects including objects and sculptures, bonus material, chapter selection control, play controls, editing controls, user selectable options and/or controls, director commentary, a virtual tour of a set (e.g., a movie set), a behind-the-scenes tour (e.g., with the content creator physically walking a user through the scenes in the virtual space as an avatar and/or performance capture of some kind), game content (e.g., mini game, video game, etc.), stage plays, virtual phone calls, chat windows, communication windows of different varieties, algorithmically generated content, animated content, flat and/or dimensionally captured performances and/or spaces, procedurally animated content, artificially intelligent animations, live and/or pre-recorded events, avatars of other users (e.g., prerecorded and/or live), and/or other content. The virtual space may include objects that are usable within the virtual space such as tools, food, a virtual currency, virtual clothing (e.g., shirt, hat, pants, etc.), a vehicle, a pet, and/or other virtual items and/or goods.

In some implementations, (e.g., according to the second mode) a user may interact with the virtual reality content presented. For example, the user may communicate with presented characters, and/or may socially interact in other ways with virtual characters and/or other users in the virtual space. Socially interacting may include communicating, chatting, playing a game, viewing virtual reality content, attending an event, and/or other socializing. This socializing may be taking place while the virtual reality content is being displayed to the user, for example, such that multiple users may interact based on the same virtual reality content. In some implementations, in the second content mode, a user may explore the virtual space and/or play a game within the virtual space. Exploring the virtual space, for example, may include user-directed movement through the virtual space such that the location and/or viewpoint of the user changes based on his movement.

In some implementations, the virtual reality content may be similarly presented to the user via one or more screens, projection devices, three-dimensional image generation devices, light field imaging devices that project an image onto the back of a user's retina, virtual reality technology that utilizes contact lenses, virtual reality technology that communicates directly with (e.g., transmits signals to and/or receives signals from) the brain, and/or other devices configured to display the virtual reality content to the user.

Views of the virtual space may correspond to a location in the virtual space (e.g., a location in a scene of a story). The location may have a topography, express ongoing real-time interaction by one or more users, and/or include one or more objects body postured within the topography that are capable of locomotion within the topography. In some instances, the topography may be a two-dimensional topography. In other instances, the topography may be a three-dimensional topography. The topography may include dimensions of the space, and/or surface features of a surface or objects that are "native" to the space. In some instances, the topography may describe a surface (e.g., a ground surface) that runs through at least a substantial portion of the space. In some instances, the topography may describe a volume with one or more bodies body postured therein (e.g., a simulation of gravity-deprived space with one or more celestial bodies body postured therein). The views of the virtual space may be presented to the user such that a user may move through the virtual space and/or interact (e.g., according to the second content mode) with the virtual space as the user would move through and interact with a corresponding physical space. For example: a user may walk, jog, and/or run through the virtual space; sit down; stand up; stop and observe an object in the virtual space; look up/down/left/right/etc.; lean to look around an object in the virtual space; and/or other movements and/or interactions.

The above description of the views of the virtual space is not intended to be limiting. The virtual space may be expressed in a more limited, or richer, manner. For example, in some implementations, views determined for the virtual space may be selected from a limited set of graphics depicting an event in a given place within the virtual space. In some implementations, views determined for the virtual space may include additional content (e.g., text, audio, pre-stored video content, and/or other content) that describes, augments, and/or overlays particulars of the current, previous, and/or future state of the place.

Returning to FIG. 1, as described above, the virtual reality content may be presented to the user in a virtual space. In some implementations, the virtual space may be hosted by a server over a network, such as the Internet. The virtual space may be accessed by users via computing devices, such as computing device 12 (e.g., computing device 12 may be a client computing device). This may facilitate networked viewing of virtual reality content (e.g., a story). Multiple viewers (users) may view the same virtual reality content together at the same time, but in different locations, with their own computing devices. In other words, users who are in different physical locations may enjoy the same virtual reality content at the same time and/or access a recording of an earlier shared and/or saved experience and view it later. Such an implementation is illustrated in FIG. 3.

FIG. 3 illustrates a server 40 configured to communicate with computing device 12 via a network, in accordance with an implementation. In some implementations, server 40 may be configured to provide the virtual space by hosting the virtual space over a network, such as the Internet. Server 40 may include electronic storage, one or more processors, communication components, and/or other components. Server 40 may include communication lines, or ports to enable the exchange of information with a network and/or other computing platforms. Server 40 may include a plurality of hardware, software, and/or firmware components operating together to provide the functionality attributed herein to server 40. For example, server 40 may be implemented by a cloud of computing platforms operating together as server 40.

Server 40 may be configured to execute computer-readable instructions for implementing an instance of the virtual space and to facilitate the participation of one or more users in the virtual space. For example, server 40 may be configured such that one or more users may be presented with the same virtual reality content and/or have the same experience while in the virtual space. In some implementations, server 40 may be configured such that one viewer in a networked and/or otherwise linked group of viewers viewing the same content is designated as a leader and controls playback for the entire group, (e.g., automatically resuming playback for individual user's computing devices when the leader resumes). Server 40 may be configured such that the leader may also engage any other controls for the entire group, including but not limited to program options and/or playback control beyond play and pause functions. In some implementations, server 40 may be configured such that, responsive to one or more individual users (the specific number of users may be pre-set by a content creator for example, and/or determined in other ways) in a group of users viewing the same content changing his body posture, the content may be paused and/or resumed as appropriate. Individual users may access server 40 and/or the virtual space via computing device 12, for example. Server 40 may be configured to communicate virtual space information (e.g., streaming visual information, object/body posture information, and/or other information) to computing device 12 for presentation to the user and/or to other client computing platforms and/or other users. Server 40, computing device 12, and/or external resources 300 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server 40, computing device 12, and/or external resources 300 may be operatively linked via some other communication media. In some implementations, the virtual space may include an "offline" version of the virtual space. For example, the virtual space may be hosted locally on computing device 12.

External resources 300 may include sources of information that are outside of system 10 (as shown in FIG. 1), external entities participating with system 10, motion simulators configured to integrate and/or be used with system 10, and/or other resources. In some implementations, some or all of the functionality attributed herein to external resources 300 may be provided by resources included in system 10.

Returning to FIG. 1, sensor(s) 18 may be configured to generate output signals conveying information related to a body posture of the user in physical space and/or other information. The body posture of the user may refer to a physical position in which the user's body is oriented and/or the physical position of the limbs and/or the carriage of the user's body. In some implementations, body posture may include the position of one or more extremities in relation to the body. For example, body posture may include one or more of sitting, standing, reclining, kneeling, lifting one or more extremities (e.g., a hands-lifted body posture), lying, squatting, a position of one or more extremities (e.g., hands in lap), and/or other body postures. In some implementations, body posture may include body language (e.g., a relaxed body language and/or an interactive body language). In some implementations, system 10 may implement a calibration procedure (e.g., manual/prompted and/or automatic/unprompted) with sensor(s) 18 to determine calibrations and/or thresholds for determining a given user's body posture (e.g., because two people may sit and/or stand differently).

Sitting may be defined as a body posture in which the user's weight is supported by his thighs and/or buttocks. While sitting, a user's back may be upright such that the user's thighs and the user's trunk form an angle less than 180 degrees. In some implementations, the user's thighs and trunk may form an angle between 70 degrees and 110 degrees while sitting. By way of example, while sitting, the user's shoulders may be vertically aligned and/or close to aligned with the user's hips, and the user's knees may be offset in front of the user. Standing may be defined as the user being in an upright posture on his feet. For example, while standing one or both of the user's feet, one or both of the user's knees, the user's trunk, and/or one or both of the user's shoulders may be aligned. When standing, the user's weight may be supported by the user's feet.

Reclining may be defined as a body posture wherein one or more of the user's thighs, buttocks, and/or back support the user's weight. In a reclined posture, the user may lean and/or lay back in a relaxed posture against a sloping back support (e.g., a reclined chair). Kneeling may include a body posture in which the user goes down onto and/or rests on one or more of his knees. While kneeling, the user's weight may be supported by one or more of the user's knees. Lifting one or more extremities may include lifting one or more hands, arms, feet, legs, and/or other extremities into the air and/or from a resting posture. Raised hands may include hands that are moved up towards the user's head from a previous position at the user's hips, sides, in the user's lap, and/or other resting locations. Raised hands may be raised to, or above the user's shoulders, and/or between the user's shoulders and the user's hips when the user is standing. While sitting or reclining, raised hands may include hands raised off of a user's lap, furniture, and/or other resting surface. For example, a user may be able to change the content mode while sitting, laying, and/or standing by raising and/or moving their hands and/or arms. By way of a non-limiting example, the user may bring their hands and/or arms into a ready and/or interactive posture (e.g., raised, in front of their body, and/or otherwise ready to interact) from a resting posture to initiate a change in content mode from passive to interactive. Continuing the non-limiting example, responsive to the user returning to their hands and/or arms to a resting posture, the content mode may change back to a passive content mode.

A lying body posture may include a horizontal position of the user's body. In some implementations, a user may lie horizontally on their back, stomach, and/or side in a resting position and/or interactive position. By way of non-limiting example, the user may have lying down posture while experiencing primary virtual reality content according to the first mode (e.g., flying through a story) and may raise his arms and/or hands to initiate the second content mode and interact with the secondary virtual reality content. A squatting body posture may include a crouched body position. While squatting, a user may be on his feet with his knees bent such that the buttocks rest on or near the user's heels.

Figure 4A:
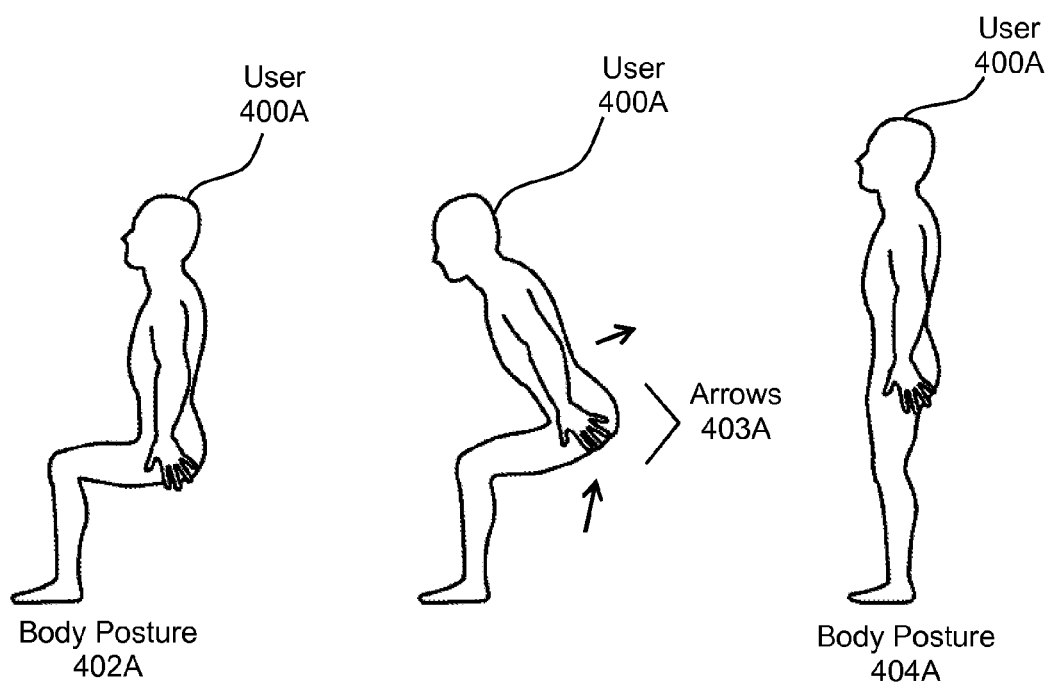
FIGS. 4A-4C illustrate first body postures and second body postures of a user, in accordance with some implementations.
Figure 4B:
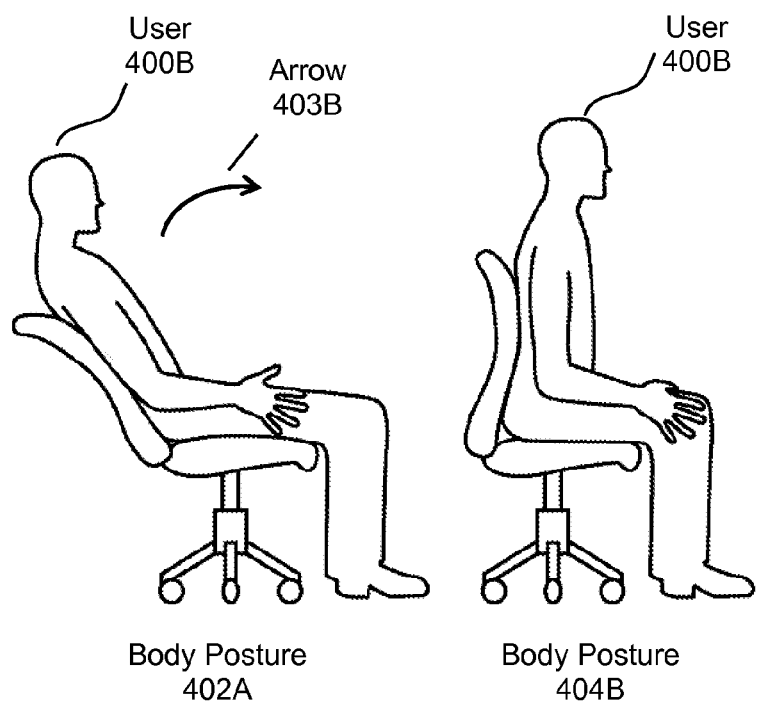
Figure 4C:
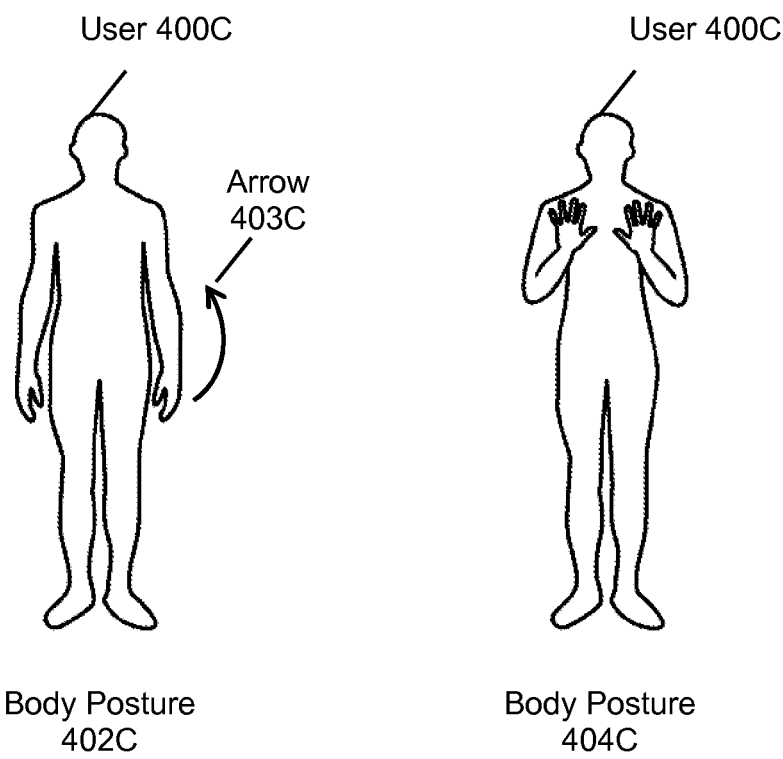

FIGS. 4A-4C illustrate first body postures and second body postures of user 400, in accordance with some implementations. User 400 may be the same as or similar to user 200 illustrated in FIG. 2. In some implementations, as illustrated in FIG. 4A, a first body posture 402A of user 400A may include sitting. In some implementations, for example, User 400 may sit on a stool, chair, bench, floor, and/or other sitting surface (e.g., not pictured in FIG. 4A, see e.g., FIG. 4B chair 405). A second body posture 404A of user 400A may include standing. As such, responsive to user 400A having a first body posture 402A, primary virtual reality content may be presented to user 400A according to a first content mode. User 400A may change his body posture from first body posture 402A to second body posture 404A by lifting his buttocks and/or shifting his weight to be supported by his feet, in accordance with the direction of arrows 403A. Responsive to user 400A changing his body posture from first body posture 402A to second body posture 404A, the content mode may change and/or the secondary virtual reality content may be presented to user 400A according to a second content mode.

In some implementations, as illustrated in FIG. 4B, a first body posture 402B of user 400B may include user 400B reclining. In some implementations, User 400B may be reclining in chair 405. A second body posture 404B of user 400B may include user 400B sitting such that his back is upright instead of leaning back in a reclined position. In some implementations, User 400B may be sitting upright in chair 405. As such, responsive to user 400B having a first body posture 402B, the primary virtual reality content may be presented to the user according to a first content mode. User 400B may change his body posture from first body posture 402B to second body posture 404B by bringing his shoulders forward such that his back is mostly upright, in accordance with the direction of arrow 403B. Responsive to user 400B changing his body posture from first body posture 402B to second body posture 404B, the content mode may change and/or the secondary virtual reality content may be presented to user 400B according to a second content mode.

In some implementations, as illustrated in FIG. 4C, a first body posture 402C of user 400C may include user 400C standing with his hands at his side. A second body posture 404C of user 400A may include user 400C standing with his hands raised and/or lifted. As such, responsive to user 400C having a first body posture 402C, the primary virtual reality content may be presented to the user according to a first content mode. User 400C may change his body posture from first body posture 402C to second body posture 404C by raising his hands and/or arms in accordance with the direction of arrow 403C. Responsive to user 400C changing his body posture from first body posture 402C to second body posture 404C, the content mode may change and/or the secondary virtual reality content may be presented to user 400C according to a second content mode.

Returning to FIG. 1, sensor(s) 18 may be configured to generate output signals conveying information related to any number of different body postures, positions, and/or orientations of the user. In some implementations, sensor(s) 18 may include one or more of a GPS sensor, a gyroscope, an accelerometer, an altimeter, a compass, a camera-based sensor (e.g., used in connection with, a magnetic sensor, an optical sensor, an infrared sensor, a radar sensor, a motion-tracking sensor, an inertial sensor, a CCB sensor, an eye-tracking sensor, a facial-tracking sensor, a body-tracking sensor (e.g., one or more arm-, hand-, leg-, and/or foot-tracking sensors and/or other tracking sensors), and/or other sensors. It should be noted that the description of sensor(s) 18 provided herein is not intended to be limiting. Rather, the description of sensor(s) 18 is intended to include future evolutions of sensor and/or controller technology.

User interface 14 may be configured to provide an interface between system 10 and the user through which the user may provide information to and receive information from system 10. This enables data, cues, results, and/or instructions and any other communicable items, collectively referred to as "information," to be communicated between the user and system 10. By way of a non-limiting example, user interface 14 may be configured to display the virtual reality content to the user. Examples of interface devices suitable for inclusion in user interface 14 include a touch screen, a keypad, touch-sensitive and/or physical buttons, switches, a keyboard, knobs, levers, a display (e.g., display 16), speakers, a microphone, an indicator light, a printer, and/or other interface devices. In some implementations, user interface 14 includes a plurality of separate interfaces (e.g., multiple displays 16). In some implementations, user interface 14 includes at least one interface that is provided integrally with processor(s) 20. In some implementations, user interface 14 may be included in computing device 12 (e.g., a desktop computer, a laptop computer, a tablet computer, a smartphone, a virtual reality headset, etc.) associated with an individual user. In some implementations, user interface 14 may be included in a first computing device (e.g., a virtual reality headset) that is located remotely from a second computing device (e.g., server 40 shown in FIG. 3).

It is to be understood that other communication techniques, either hard-wired or wireless, are also contemplated by the present disclosure as user interface 14. For example, the present disclosure contemplates that user interface 14 may be integrated with a removable storage interface provided by electronic storage 30. In this example, information may be loaded into system 10 from removable storage (e.g., a smart card, a flash drive, a removable disk) that enables the user to customize the implementation of system 10. Other exemplary input devices and techniques adapted for use with system 10 as user interface 14 include, but are not limited to, an RS-232 port, an RF link, an IR link, a modem (telephone, cable or other), a USB port, Thunderbolt, a Bluetooth connection, and/or other input devices and/or techniques. In short, any technique for communicating information with system 10 is contemplated by the present disclosure as user interface 14.

Display 16 may be configured to present the virtual reality content to the user. Display 16 may be configured to present the virtual reality content to the user according to content modes. Content modes may define the manner in which the virtual reality content is presented to the user, the manner in which the user interacts with the virtual reality content, and/or other controls/information that may affect the user's experience with the virtual reality content. Display 16 may be controlled by processor(s) 20 to present the virtual reality content to the user such that the presented virtual reality content includes primary virtual reality content, secondary virtual reality content, intermediary virtual reality content, and/or other virtual reality content that may be presented according to one or more content modes. Display 16 may include one or more screens, projection devices, three-dimensional image generation devices, light field imaging devices that project an image onto the back of a user's retina, virtual reality technology that utilizes contact lenses, virtual reality technology that communicates directly with (e.g., transmitting signals to and/or receiving signals from) the brain, and/or other devices configured to display the virtual reality content to the user. The one or more screens and/or other devices may be electronically and/or physically coupled, and/or may be separate from each other. As described above, in some implementations, display 16 may be included in a virtual reality headset worn by the user. In some implementations, display 16 may be a single screen and/or multiple screens included in a computing device 12 (e.g., a cellular telephone, a smartphone, a laptop, a tablet computer, a desktop computer, a television set-top box/television, smart TV, a gaming system, a virtual reality headset, and/or other devices). In some implementations, display 16 may include a plurality of screens physically arranged about a user such that when a user looks in different directions, the plurality of screens presents individual portions (e.g., that correspond to specific view directions and/or fields of view) of the virtual reality content to the user on individual screens.

Processor(s) 20 may be configured to provide information processing capabilities in system 10. Processor(s) 20 may communicate wirelessly with user interface 14, sensor(s) 18, electronic storage 30, external resources not shown in FIG. 1, and/or other components of system 10. In some implementations, processor(s) 20 may communicate with user interface 14, sensor(s) 18, electronic storage 30, external resources not shown in FIG. 1, and/or other components of system 10 via wires. In some implementations, processor(s) 20 may be remotely located (e.g., within server 40 shown in FIG. 3) relative to user interface 14, sensor(s) 18, electronic storage 30, external resources not shown in FIG. 1, and/or other components of system 10.

Processor(s) 20 may be configured to execute computer program components. The computer program components may be configured to enable an expert and/or user to interface with system 10 and/or provide other functionality attributed herein to user interface 14, sensor(s) 18, electronic storage 30, and/or processor(s) 20. The computer program components may include a body posture component 22, a content mode component 24, a display component 26, an interaction component 28, and/or other components.

Processor(s) 20 may comprise one or more of a digital processor, an analog processor, a digital circuit designed to process information, an analog circuit designed to process information, a state machine, and/or other mechanisms for electronically processing information. Although processor(s) 20 is shown in FIG. 1 as a single entity, this is for illustrative purposes only. In some implementations, processor(s) 20 may comprise a plurality of processing units. These processing units may be physically located within the same device (e.g., a server, a desktop computer, a laptop computer, a tablet computer, a smartphone, a virtual reality headset, and/or other computing devices), or processor(s) 20 may represent processing functionality of a plurality of devices operating in coordination (e.g., a plurality of servers, a server and a computing device 12). Processor(s) 20 may be configured to execute components 22, 24, 26, and/or 28 by software; hardware; firmware; some combination of software, hardware, and/or firmware; and/or other mechanisms for configuring processing capabilities on processor(s) 20.

It should be appreciated that although components 22, 24, 26, and 28 are illustrated in FIG. 1 as being co-located within a single processing unit, in implementations in which processor(s) 20 comprises multiple processing units, one or more of components 22, 24, 26, and/or 28 may be located remotely from the other components (e.g., such as within server 40 shown in FIG. 3). The description of the functionality provided by the different components 22, 24, 26, and/or 28 described herein is for illustrative purposes, and is not intended to be limiting, as any of components 22, 24, 26, and/or 28 may provide more or less functionality than is described. For example, one or more of components 22, 24, 26, and/or 28 may be eliminated, and some or all of its functionality may be provided by other components 22, 24, 26, and/or 28. As another example, processor(s) 20 may be configured to execute one or more additional components that may perform some or all of the functionality attributed below to one of components 22, 24, 26, and/or 28. In some implementations, one or more of components 22, 24, 26, and/or 28 may be executed by a processor incorporated in a remotely located server, and/or other components of system 10.

Body posture component 22 may be configured to determine the body posture of the user based on the output signals from sensor(s) 18 and/or based on other information. The body posture of the user may refer to a physical position in which the user's body is oriented and/or the physical position of the limbs and/or the carriage of the user's body as described herein. Determining the body posture of the user based on the output signals may include determining when the body posture of the user changes (e.g., a user may change his body posture from the first body posture to the second body posture). Determining when the body posture of the user changes may include determining a point at which at least one parameter of the user's body posture falls outside of the parameters a first body posture, second body posture, and/or third body posture and within the parameters of another body posture (e.g., the first body posture, the second body posture, the third body posture, and/or other body postures). One or more thresholds may define a point at which a change in body posture is determined. In some implementations, a delta and/or change in a user's body posture may be used determine when the body posture of a user changes. The delta may be large enough to enable a user to move around a little bit. For example, a user may slightly move (e.g., lean one or more directions, adjust their body, and/or make other movements) without triggering (e.g., causing the system to determine) a change in body posture.

For example, the user's body posture may change from sitting to standing at the moment a majority of the user's weight (e.g., detected based on signals related to pressure and/or other output signals) is supported by the user's feet. By way of another example, the user's body posture may change from sitting to standing at the moment the user's hips vertically align, and/or approach vertical alignment, with the user's shoulders (e.g., detected based on signals from one or more body position/posture sensors), and the user is on his feet. By way of another example, the user's body posture may change from sitting to standing at the moment the user lifts his buttocks in an upward and/or forward motion (e.g., detected based on signals related to motion and/or other output signals). In some implementations, for example, a user's body posture may change from reclining to sitting up when the angle between the user's thighs and trunk changes from greater than 110 degrees to in between 70 degrees and 110 degrees (e.g., detected based on signals related to motion, position, and/or other output signals). In some implementations, for example, a user's body posture may change from standing with his hands at his side to the user standing with his hands slightly raised when the user's hands are lifted in an upward motion (e.g., detected based on signals related to motion, position, and/or other output signals). Other non-limiting examples for detecting when a user's body position changes and/or determining a change in content mode may include: detection systems and/or components that use the body language of the user; detection systems and/or components that use a combination of inputs involving silhouette, body language, momentum information, degree of lean, amount of body weight supported by a user's feet versus his posterior, and/or height; detection systems and/or components using established sitting or standing boundaries (e.g., thresholds) in the real world; and/or other detection and/or determination systems and/or components.

Content mode component 24 may be configured to determine a content mode based on the body posture of the user (e.g., the body postured determined by body posture component 122). Content mode component 24 may be configured to determine a content mode according to which display component 26 may cause display 16 to present the virtual reality content to the user. The content mode may define the manner in which the virtual reality content is presented to the user, the manner in which the user interacts with the virtual reality content, and/or other controls/information that may affect the user's experience with the virtual reality content. In some implementations, primary virtual reality content may be presented to the user according to the first content mode. The first content mode may include a passive content mode wherein the primary virtual reality content that is presented to the user according to the first content mode may include passive virtual reality content as further described herein. In some implementations, secondary virtual reality content may be presented to the user according to the second content mode. The second content mode may include an interactive content mode wherein the secondary virtual reality content presented to the user according to the second content mode may include interactive virtual reality content as further described herein. In some implementations, the intermediary virtual reality content may be presented to the user according to a third (e.g., intermediary content mode).

In some implementations, content mode component 24 may be configured such that a user may change his content mode by using one or more controls provided via user interface 14 and/or other controls. For example, the user may use a pointer (a physical pointer such as a mouse and/or other pointer and/or a virtual pointer displayed in the virtual space), a gaming-type controller, and/or other controllers to indicate his desire to change content modes. In some implementations, the one or more controls provided via user interface 14 may include gesture-based controls (e.g., swiping; pinching; expanding a pinch; moving a hand, arm, and/or other body parts; making a specific motion with a body part; etc.)

Display component 26 may be configured to cause display 16 to present primary virtual reality content, secondary virtual reality content, intermediary virtual reality content, and/or other virtual reality content to the user. Primary virtual reality content, secondary virtual reality content, intermediary virtual reality content, and/or other virtual reality content may include augmented reality content. Display component 26 may be configured to cause display 16 to present the primary virtual reality content, the secondary virtual reality content, intermediary virtual reality content, and/or other virtual reality content according to the determined content mode. Primary virtual reality content may include passive virtual reality content as described herein. For example, primary virtual reality content may include one or more of movies, stories, narratives, performances, virtual events, simulated physical world settings, characters, objects, collaborative projects including objects and sculptures, bonus material, chapter selection control, editing controls, director commentary, a virtual tour of a (e.g., movie) set, a behind-the-scenes tour (e.g., with the content creator physically walking a user through the scenes in the virtual space as an avatar and/or performance capture of some kind), stage plays, algorithmically generated content, animated content, flat and/or dimensionally captured performances and/or spaces, procedurally generated animated content, artificially intelligent animations, live and/or pre-recorded events, avatars of other users (e.g., prerecorded and/or live), and/or other virtual reality content that may be presented to the user from a creator dictated location. The creator dictated location may describe a location relative to the action and/or virtual reality content.

Secondary virtual reality content may include interactive virtual reality content such as, for example, interactive narratives, interactive movies, interactive stories, virtual events, video games, interactive games, simulated physical world settings, characters, objects, collaborative projects including objects and sculptures, bonus material, interaction/movement controls, game controls, virtual phone calls, chat windows, communication windows of different varieties, algorithmically generated content, animated content, flat and/or dimensionally captured performances and/or spaces, procedurally generated animated content, artificially intelligent animations, live and/or pre-recorded events, avatars of other users (e.g., prerecorded and/or live), and/or other virtual reality content that a user may interact with.

Display component 26 may be configured to facilitate a user experience between the user and the virtual reality content presented. The user experience may be facilitated based on the content mode. Facilitating the user experience may include causing the display (e.g., display 16) to present the virtual reality content according to the content mode. In some implementations, responsive to the body posture of the user corresponding to the first body posture, the first content mode may be determined. Based on the first content mode being determined, display component 26 may be configured to present the primary virtual reality content to the user according to the first content mode via display 16. In some implementations, responsive to the body posture of the user corresponding to the second body posture, the second content mode may be determined. As such, the content mode determined by content mode component 24 may change from the first content mode to the second content mode such that display component 26 may be configured to present the secondary virtual reality content to the user according to the second content mode. By way of example, the first user's body posture may include sitting and the second user body posture may include standing. In some implementations, display component 26 may be configured to cause display 16 to pause the presentation of the primary virtual reality content responsive to the body posture of the user changing from the first body posture to the second body posture (e.g., sitting to standing, reclining to sitting, standing with hands at the sides to standing with hands raised/lifted, and/or other body postures). In some implementations, responsive to the body posture of the user changing from the second body posture back to the first body posture, display component 26 may cause the presentation of the primary virtual reality content to be resumed based on a determination by content mode component 24 such that the content mode is changed from the second content mode to the first content mode.

In some implementations, system 10 may be configured such that a user may manually pause the presentation of the primary and/or secondary virtual reality content (e.g., via user interface 14). For example, system 10 may be configured such that a user may pause, stop, play, rewind, and/or otherwise have typical video playback control over the (primary, secondary, intermediary, etc.) virtual reality content via user interface 14. In some implementations, primary virtual reality content may be displayed with and/or at the same time as secondary virtual reality content.

In some implementations, the first content mode and/or the second content mode may be available throughout the duration of the presentation of the virtual reality content. In some implementations, the second content mode may be available at various points during the duration of the presentation of the virtual reality content. Display component 26 may be configured to cause display 16 and/or other components of system 10 to provide one or more sensory cues (e.g., an icon display) to the user responsive to an available change in content modes (e.g., where the second, interactive content mode may be available). For example, an icon displayed may indicate a change in posture the user should replicate and/or another call to action to change the content mode and cause interactive virtual reality content (e.g., secondary virtual reality content) to be presented. Display component 26 may be configured to cause display 16 and/or other components of system 10 to provide a sensory cue(s) to the user responsive to the primary virtual reality content progressing to one or more predefined points where secondary virtual reality content may be available and/or the content mode may be switched from the first content mode to the second content mode.

In some implementations, the one or more sensory cues may comprise a pause in the primary virtual reality content, a slowing to a stop of the primary virtual reality content, a visually perceptible darkening of the primary virtual reality content, an icon within the primary and/or secondary virtual reality content, and/or other visual cues. For example, system 10 may be configured to display a story (e.g., primary virtual reality content) to the user while the user is sitting. While watching the story (e.g., a movie), an icon (e.g., an elf and/or other character/icon) may be presented within the virtual space. When the user stands, the story may be paused and/or the user may be able to interact with secondary virtual reality content (e.g., by playing a game, exploring the virtual reality content, influencing the virtual reality content, and/or otherwise interacting with the virtual reality content). In some implementations, display component 26 may be configured to cause other sensory cues (e.g., via other components of user interface 14, and/or external resources 300 (as shown in FIG. 3)) to be provided to the user. Other sensory cues may include other visual cues (e.g., a flashing visual indicator that is part of user interface 14), auditory cues, somatosensory cues (e.g., tactile cues such as a virtual reality headset vibration, vibration of a surface the user is physically standing on, etc.), olfactory cues (e.g., a scent produced by external resources 300), haptic feedback, climate adjustment cues (e.g., heated and/or cooled air delivered to the user), weather-related cues (e.g., changes in virtual weather from one weather condition to another such as sun, rain, wind, snow, sleet, etc.), motion simulation (e.g., as from a motion simulator) and/or actual physical motion cues (e.g., physically rotating and/or otherwise moving in different directions by controlling external equipment associated with system 10), and/or other sensory cues. In some implementations, display component 26 may be configured to cause display 16 and/or other components of system 10 to vary an intensity of an individual cue and/or provide more than one cue at a time.

In some implementations, such as when computing device 12 is a virtual reality headset, display component 26 may be configured to cause display 16 to stop and/or pause presenting the virtual reality content to the user responsive to the user removing the virtual reality headset from his head. For example, sensor(s) 18 may be configured to generate output signals that convey information that indicates whether the user is wearing the virtual reality headset. Display component 26 may be configured to cause display 16 to cease presenting the virtual reality content responsive to the information conveyed by the output signals indicating that the user is no longer wearing the virtual reality headset.

In some implementations, display component 26 may be configured to cause display 16 to resume (e.g., automatically) presenting the virtual reality content to the user responsive to the user replacing the virtual reality headset on his head. The virtual reality content may resume from the point where it left off when the headset was removed. In some implementations, display component 26 may be configured to cause display 16 to automatically present the virtual reality content to the user responsive to the user placing the virtual reality headset on his head for the first time. In some implementations, the virtual reality content may re-start from the beginning of the virtual reality content, re-start from where it left off when the headset was removed, re-start from a content creator specified start point, and/or from other points. This may be defined by the content creator, for example.

Interaction component 28 may be configured to facilitate a user experience between the user and the secondary virtual reality content. Facilitating the user experience between the user and the secondary virtual reality content based on the second content mode may include facilitating one or more interactions between the user and the secondary virtual reality content interaction between the user and the secondary virtual reality content responsive to the second content mode being determined by content mode component 24. The secondary virtual reality content may be presented according to the second content mode such that the user may interactively experience (e.g., via moving around, walking, running, flying, exploring, playing, etc.) the secondary virtual reality content. Interactively experiencing the secondary virtual reality content may include viewing and/or interacting with the secondary virtual reality content from a user-directed location and/or viewpoint (e.g., a viewpoint that changes based on the user's interaction), and/or impacting behaviors of entities represented in the secondary virtual reality content. In some implementations, interaction in the second content mode may include facilitating control of virtual space entities (characters, objects, etc.), control of simulated physical phenomena (e.g., wind, rain, earthquakes, and/or other phenomena), control of a scene and/or a setting in the virtual space, and/or control over other elements included in the secondary virtual reality content, within the virtual space, and/or other virtual reality content presented to the user.

Interaction may include conversing (e.g., textual chatting, voice communication, etc.) with and/or otherwise socializing with virtual characters such as avatars, other characters, and/or other users. For example, interaction component 28 may be configured to facilitate communication via chat applications that utilize pop-up windows and/or pop-up avatars, pop-up point cloud video chat, and/or otherwise to allow a user to quickly respond to social media messages, and/or take a "phone call" and then automatically resume viewing content when finished. In some implementations, interacting with "off stage" characters may be an out of narrative (e.g., primary virtual reality content) function. Interaction may include moving, creating, and/or customizing objects and/or other elements in the virtual space by the user (e.g., based on information received via computing device 12 and/or other information).

Interaction may include participating in an instance of the virtual space (e.g., a scene in a story) by controlling one or more available user controlled entities in the virtual space. Such control may be exercised through control inputs and/or commands input by the user through computing device 12, for example. Interaction may include exploring one or more areas of the virtual space. Interaction may include interacting and/or impacting behaviors of a specific character, object, and/or location in the virtual space; making facial expressions that express an attitude toward a specific character, object, and/or location in the virtual space; and/or other interaction (e.g., determined based on output signals from eye tracking, facial tracking, brain wave, body tracking sensors, and/or other sensors included in sensor(s) 18).

Interaction component 28 may be configured such that interaction includes handshakes, exchanges of goods, physical fights, side adventures with a particular character, travel and/or flight with characters and/or objects, moving objects and/or characters, knocking things over, picking things up, damaging objects in the virtual space, creating graffiti, blasting the objects, characters, and/or other features of the virtual space with different elements such as forces of nature (e.g., wind, rain, snow, fire, etc.) and/or other elements, solving puzzles, taking notes, storing found objects, altering the virtual space in any way, causing system 10 to replay a particular portion of virtual reality content, causing system 10 to rewind the virtual reality content to a particular point in time, and/or other interaction. In short, any control of the virtual space, communication with characters in the virtual space, creation and/or customization of objects in the virtual space, movement within the virtual space (e.g., moving to and/or through any particular portion and/or view of the virtual space such as flying through a cave), a change of virtual environment altogether, an interaction and/or movement that has a dynamic active and/or passive effect on the virtual space and/or characters within the virtual space, collaborative projects (e.g., collaborative story experiences and/or future forward interactive (including collaborative) story editing and/or creating experiences), and/or other interaction may be facilitated by interaction component 28.

In some implementations, interaction component 28 may be configured to adjust the primary virtual reality content presented to the user based on interaction between the user and the secondary virtual reality content in the second content mode, and/or based on other information. For example, the storyline of a primary virtual reality content narrative (e.g., a story and/or movie) may be adjusted based on and experience and/or interaction between the user and secondary virtual reality content. In some implementations, interaction component 28 may be configured to adjust the secondary virtual reality content presented to the user based on a progression of the user through the primary virtual reality content (e.g., progression through a story watched by the user) and/or other information.

By way of a non-limiting example, the primary virtual reality content may be presented to the user according to the first content mode such that the user may be able to watch the primary virtual reality content from a creator dictated location while the user is sitting. If the user wants to interact with secondary virtual reality content associated with the primary virtual reality content (e.g., interact with the virtual space presented in the narrative and/or other passive virtual reality content), the user may stand. Responsive to the user standing, the second content mode may be determined and the content mode may change from the first content mode to the second content mode such that secondary virtual reality content is presented to the user. The user may experience and/or interact with the secondary virtual reality content (e.g., by interactively exploring a virtual space associated with and/or corresponding to a scene presented in the narrative) until he wants to sit back down causing the primary content to resume presentation.

By way of a second non-limiting example, the primary virtual reality content may be a story (e.g., a movie) and the secondary virtual reality content may be a video game and/or mini-game that takes place on an expanded set of the primary virtual reality content story. The expanded set of the video game and/or mini-game may change over time as the user progresses through the primary virtual reality content story, for example. Or, vice versa, as the user progresses through the video game and/or mini game, changes to the primary virtual reality content story are made that reflect progress through the game. As such, the story may be presented to the user according to the first content mode such that the user may be able to watch the story while the user is sitting. If the user wants to play the video game and/or mini-game, the user may stand up and/or otherwise change his body posture. Other non-limiting examples are contemplated.

Customization, and/or adjustment of the virtual reality content modes, the virtual reality content, the body posture(s), and/or other characteristics of system 10 may include coupling and/or defining one or more body postures to correspond with one or more specific content modes and/or virtual reality content; creating virtual reality content (e.g., characters, objects, a scene, etc.); customizing and/or adjusting an appearance of virtual reality content; customizing and/or adjusting actions performed by virtual reality content; creating, adjusting, and/or customizing relationships and/or transitions between the first content mode and the second content mode; specifying the type of sensory cue(s) used to indicate to a user that another content mode may be available, specifying an intensity level of the sensory cue(s) so that the sensory cue is adjusted to the user's liking, and/or other creation, customization, and/or adjustment of virtual reality content and/or other components of system 10. In some implementations, interaction component 28 may be configured such that a user may create, customize, and/or adjust within previously determined parameters for creating, customizing, and/or adjusting (e.g., the previously determined parameters determined by a content creator at manufacture/during software creation).

Electronic storage 30 may comprise electronic storage media that electronically stores information. The electronic storage media of the electronic storage may include one or both of storage that is provided integrally (i.e., substantially non-removable) with the respective device and/or removable storage that is removably connectable to the respective device. Removable storage may include for example, a port or a drive. A port may include a USB port, a firewire port, and/or other port. A drive may include a disk drive and/or other drive. Electronic storage may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storage may include one or more virtual storage resources (e.g., cloud storage, a virtual private network, and/or other virtual storage resources). Electronic storage may store files, software algorithms, information determined by processor(s) 20, and/or other information that enables the respective devices to function as described herein.

Figure 5:
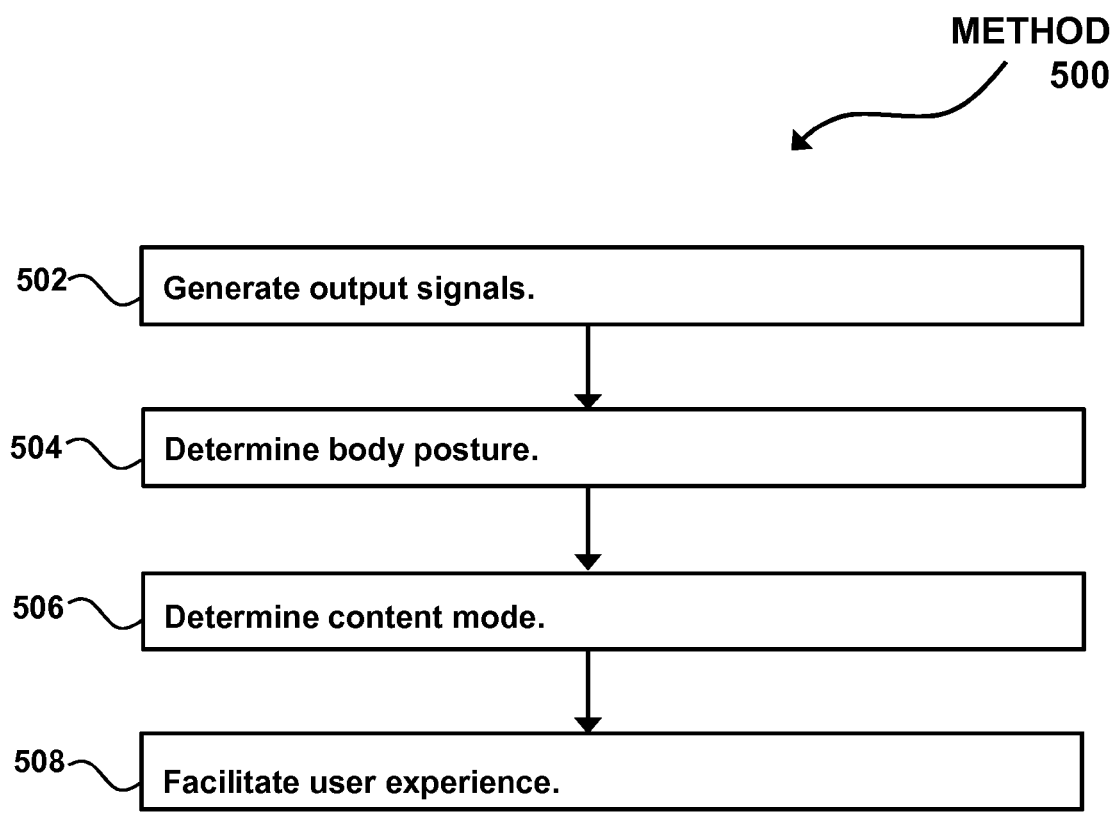
FIG. 5 illustrates an implementation of a method for presenting virtual reality content to a user, in accordance with an implementation.

FIG. 5 illustrates an implementation of a method 500 for presenting virtual reality content to a user, in accordance with an implementation. The operations of method 500 presented below are intended to be illustrative. In some implementations, method 500 may be accomplished with one or more additional operations not described, and/or without one or more of the operations discussed. Additionally, the order in which the operations of method 500 are respectively illustrated in FIG. 5 and described below is not intended to be limiting.

In some implementations, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, output signals may be generated. The output signals may convey information related to a body posture of the user in physical space. The body posture may include a first body posture and/or a second body posture. The first body posture may correspond to the user sitting and/or the second body posture may correspond to the user standing. In some implementations, operation 502 may be performed by one or more sensors that are the same as or similar to sensor(s) 18 (shown in FIG. 1 and described herein).

At an operation 504, a body posture of the user may be determined. The body posture of the user may be determined based on the output signals and/or other information. In some implementations, operation 504 may be performed by a computer processor component that is the same as or similar to body posture component 22 (shown in FIG. 1 and described herein).

At an operation 506, a content mode may be determined. The content mode may be determined based on the body posture of the user. Content modes may define the manner in which the virtual reality content is presented to the user, the manner in which the user interacts with the virtual reality content, and/or other controls/information that may affect the user's experience with the virtual reality content. The virtual reality content may include primary virtual reality content that is presented to the user according to a first content mode and/or secondary virtual reality content that is presented to the user according to a second content mode. In some implementations, for example, the first content mode may be a passive content mode and/or the second content mode may be an interactive content mode. Operation 506 may be performed by computer processor components that are the same as or similar to content mode component 24 (shown in FIG. 1 and described herein).

At operation 508, a user experience may be facilitated based on the content mode. The user experience may be facilitated by causing the display to present the virtual reality content. The content may be presented according to the determined content mode. For example, the first content mode may be determined responsive to the body posture of the user corresponding to the first body posture (e.g., sitting). Responsive to the first content mode being determined, the primary virtual reality content may be presented to the user according to the first content mode. The second content mode may be determined responsive to the body posture of the user corresponding to the second body posture (e.g., standing). Responsive to the second content mode being determined, the secondary virtual reality content may be presented to the user according to the second content mode.

For example, the primary virtual reality content may be passive virtual reality content such as a story (e.g., a three-dimensional movie) and/or the secondary virtual reality content may be interactive virtual reality content associated with the story (e.g., views/scenes from a story that may be explored, characters and/or objects from the story that the user may interact with, interactive virtual reality content with music and/or a soundtrack from the story, a game associated with the story, etc.). The virtual reality content for display to the user may be obtained from electronic storage, via external resources not included in system 10 (e.g., a server), and/or from other sources.

For example, the primary virtual reality content may include passive virtual reality content such as a music video and/or the secondary virtual reality content may be interactive virtual reality content associated with the music video such that the user may interact with the music video by changing his body posture from a first body posture to a second body posture. In some implementations, the virtual reality content may be obtained from the internet.

In some implementations, facilitating a user experience between the user and the virtual reality content presented may include causing a display to present the virtual reality content according to a determined content mode. In some implementations, the display may be included in a virtual reality headset worn by the user. The display may be caused to display the virtual reality content based on the determined content mode and/or the user's body posture such that the primary virtual reality content may be presented to the user responsive to the user's body posture corresponding to a first body posture and/or the secondary virtual reality content may be presented to the user responsive to the user's body posture corresponding to a second body posture. In some implementations, facilitating a user experience between the user and the secondary virtual reality content presented may include facilitating interaction between the user and the second virtual reality content. Operation 508 may be performed by computer processor components and a display that are the same as or similar to body posture component 22, content mode component 24, display component 26, interaction component 28, and/or display 16 (shown in FIG. 1 and described herein).

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation. As another example, the present disclosure contemplates that technological advances in display technology such as light field imaging on the back of a retina, contact lens displays, and/or a display configured to communicate with (e.g., transmit signals to and/or receive signals from) a user's brain fall within the scope of this disclosure.

What is claimed is:

1. A system configured to present virtual reality content to a user in a virtual space, the system comprising:
one or more sensors configured to generate output signals conveying information indicating a body posture of the user in physical space, the body posture including a first body posture and a second body posture;
a display that presents the virtual reality content to the user according to content modes that define the manner in which the virtual reality content is presented to the user and/or the manner in which the user interacts with the virtual reality content, wherein presentation of the virtual reality content via the display visually simulates presence of the user within a virtual space, the virtual space being fixed relative to physical space such that the physical position and/or view direction of the user dictates which portions of the virtual space are visible to the user, the virtual reality content comprising primary virtual reality content that is presented to the user according to a first content mode and secondary virtual reality content that is presented to the user according to a second content mode, and wherein the primary virtual reality content is presented to the user responsive to the body posture of the user corresponding to the first body position and the secondary virtual reality content is presented to the user responsive to the body posture of the user corresponding to the second body position; and
one or more physical computer processors configured by computer-readable instructions to:
determine the body posture of the user based on the output signals;
determine a content mode based on the body posture of the user;
facilitate a user experience between the user and the virtual reality content based on the content mode by causing the display to present the virtual reality content to the user according to the content mode, such that:
responsive to the body posture of the user corresponding to the first body posture, the first content mode is determined and the primary virtual reality content is presented to the user according to the first content mode; and
responsive to the body posture of the user corresponding to the second body posture, the content mode changes from the first content mode to the second content mode such that the secondary virtual reality content is presented to the user according to the second content mode, wherein the secondary virtual reality content is more interactive than the primary virtual reality content and the second content mode facilitates a higher level of interaction than the first content mode.

2. The system of claim 1, wherein the secondary virtual reality content being more interactive than the primary virtual reality content includes the secondary virtual reality content being less restrictive with respect to the user's ability to interact with the virtual reality content than the primary virtual reality content such that a level of interaction potential is higher for the secondary virtual reality content than for the primary virtual reality content.

3. The system of claim 1, wherein the first body posture includes one or more of: sitting, standing, reclining, kneeling, a hands-lifted body posture, lying, squatting, and/or a hands in lap body posture.

4. The system of claim 1, wherein the second body posture includes one or more of: sitting, standing, reclining, kneeling, a hands-lifted body posture, lying, squatting, and/or a hands in lap body posture.

5. The system of claim 1, wherein the one or more physical computer processors are configured such that the primary virtual reality content presented to the user according to the first content mode is a story.

6. The system of claim 5, wherein the one or more physical computer processors are configured such that the secondary virtual reality content is associated with the story.

7. The system of claim 1, wherein the secondary virtual reality content presented to the user according to the second content mode includes game content and/or interactive narrative content.

8. The system of claim 1, wherein responsive to the body posture of the user changing from the first body posture to the second body posture, the one or more physical computer processors are further configured by computer-readable instructions to pause the presentation of the primary virtual reality content.

9. The system of claim 8, wherein responsive to the body posture of the user changing from the second body posture to the first body posture, the one or more physical computer processors are further configured by computer-readable instructions to change from the second content mode to the first content mode such that the presentation of the primary virtual reality content is resumed.

10. The system of claim 1, wherein facilitating the user experience between the user and the secondary virtual reality content based on the second content mode includes facilitating interaction between the user and the secondary virtual reality content such that the user more actively participates with the secondary virtual reality content than with the primary virtual reality content.

11. The system of claim 10, wherein the one or more physical computer processors are further configured to adjust the primary virtual reality content presented to the user based on the interaction between the user and the secondary virtual reality content.

12. A method for presenting virtual reality content to a user in a virtual space based on body position, the method being implemented by a system including one or more sensors, a display, and one or more processors configured by machine-readable instructions, the method comprising:
  generating, via the sensors, output signals conveying information indicating a body posture of the user in physical space, the body posture including a first body posture and a second body posture;
  presenting, via the display, the virtual reality content to the user according to content modes that define the manner in which the virtual reality content is presented to the user and/or the manner in which the user interacts with the virtual reality content, wherein presentation of the virtual reality content via the display visually simulates presence of the user within a virtual space, the virtual space being fixed relative to physical space such that the physical position and/or view direction of the user dictates which portions of the virtual space are visible to the user, the virtual reality content comprising primary virtual reality content that is presented to the user according to a first content mode and secondary virtual reality content that is presented to the user according to a second content mode, and wherein the primary virtual reality content is presented to the user responsive to the body posture of the user corresponding to the first body position and the secondary virtual reality content is presented to the user responsive to the body posture of the user corresponding to the second body position;
  determining the body posture of the user based on the output signals;
  determining a content mode based on the body posture of the user;
  facilitating, via the one or more processors, a user experience between the user and the virtual reality content based on the content mode by causing the display to present the virtual reality content to the user according to the content mode, such that:
    responsive to the body posture of the user corresponding to the first body posture, the first content mode is determined and the primary virtual reality content is presented to the user according to the first content mode; and
    responsive to the body posture of the user corresponding to the second body posture, the content mode changes from the first content mode to the second content mode such that the secondary virtual reality content is presented to the user according to the second content mode, wherein the secondary virtual reality content is more interactive than the primary virtual reality content and the second content mode facilitates a higher level of interaction than the first content mode.

13. The method of claim 12, wherein the secondary virtual reality content being more interactive than the primary virtual reality content includes the secondary virtual reality content being less restrictive with respect to the user's ability to interact with the virtual reality content than the primary virtual reality content such that a level of interaction potential is higher for the secondary virtual reality content than for the primary virtual reality content.

14. The method of claim 12, wherein the first body posture includes one or more of: sitting, standing, reclining, kneeling, a hands-lifted body posture, lying, squatting, and/or a hands in lap body posture.

15. The method of claim 12, wherein the second body posture includes one or more of: sitting, standing, reclining, kneeling, a hands-lifted body posture, lying, squatting, and/or a hands in lap body posture.

16. The method of claim 12, wherein the primary virtual reality content presented to the user according to the first content mode is a story.

17. The method of claim 16, wherein the secondary virtual reality content is associated with the story.

18. The method of claim 12, wherein the secondary virtual reality content presented to the user according to the second content mode includes game content and/or interactive narrative content.

19. The method of claim 12, further comprising, responsive to the body posture of the user changing from the first body posture to the second body posture, the presentation of the primary virtual reality content.

20. The method of claim 19, further comprising changing, responsive to the body posture of the user changing from the second body posture to the first body posture, from the second content mode to the first content mode such that the presentation of the primary virtual reality content is resumed.

21. The method of claim 12, wherein facilitating the user experience between the user and the secondary virtual reality content based on the second content mode includes facilitating interaction between the user and the secondary virtual reality content such that the user more actively participates with the secondary virtual reality content than with the primary virtual reality content.

22. The method of claim 12, further comprising adjusting the primary virtual reality content presented to the user based on the interaction between the user and the secondary virtual reality content.

\* \* \* \* \*